United States Patent [19]

Marquis et al.

[11] 4,172,847

[45] Oct. 30, 1979

[54] TREATMENT OF METHYLENE-BRIDGED POLYPHENYLPOLYAMIME MIXTURES

[75] Inventors: Edward T. Marquis; Heinz Schulze, both of Austin, Tex.

[73] Assignee: Texaco Development Corp., White Plains, N.Y.

[21] Appl. No.: 522,486

[22] Filed: Nov. 11, 1974

[51] Int. Cl.$^2$ .............................................. C07C 85/26
[52] U.S. Cl. ........................ 260/570 D; 260/453 AM
[58] Field of Search ................................... 260/570 D

[56] References Cited

U.S. PATENT DOCUMENTS

| | | | |
|---|---|---|---|
| 3,362,979 | 1/1968 | Bentley | 260/570 X |
| 3,478,099 | 11/1969 | Rose et al. | 260/570 |
| 3,542,871 | 11/1970 | Thompson | 260/570 |

OTHER PUBLICATIONS

Kirk–Othmer, "Encyclopedia of Chemical Technology", 2nd ed., vol. 6, pp. 492–495 (1965).

*Primary Examiner*—Robert V. Hines
*Attorney, Agent, or Firm*—James L. Bailey

[57] ABSTRACT

A process for treating methylene-bridged polyphenylpolyamine mixtures prepared by the silica-alumina catalyzed condensation reaction of aniline and formaldehyde to obtain substantially pure low functionality Diaminodiphenylmethanes having increased 4,4'-positional isomer content and a higher functionality methylene-bridge polyphenylpolyamine mixture having a narrow molecular weight range is disclosed. A methylene-bridge polyphenylpolyamine mixture, prepared by the condensation reaction of aniline and formaldehyde carried out in the presence of a silica-alumina cracking catalyst, containing at least about 75 weight percent diaminodiphenylmethanes based upon the weight of the mixture and having a 4,4'-positional isomer content in the diamine portion of above about 65%, based upon the weight of the diamine portion, is admixed at a temperature of from about room temperature to about 150° C. with a material capable of forming a solution with the mixture at the temperature employed. A portion of the admixture-solution is then allowed to crystallize and is separated therefrom, which comprises substantially pure diaminodiphenylmethane having a 4,4'-positional isomer content of above about 85 weight percent. The remainder of the admixture contains a methylene-bridged polyphenylpolyamine mixture of reduced diaminodiphenylmethane content and a narrow molecular weight distribution. Both portions can be employed as precursors in conventional phosgenation techniques to provide corresponding organic isocyanates which are highly useful in the preparation of certain coatings, elastomers, flexible and rigid forms and the like.

7 Claims, No Drawings

TREATMENT OF METHYLENE-BRIDGED POLYPHENYLPOLYAMIME MIXTURES

BACKGROUND OF THE INVENTION

1. FIELD OF THE INVENTION

The present invention relates to the preparation of methylene-bridged polyphenylpolyamines and more particularly pertains to the treatment of methylene-bridged polyphenylpolyamine mixtures prepared by the silica-alumina catalyzed condensation reaction of aniline and formaldehyde.

2. DESCRIPTION OF THE PRIOR ART

The preparation of methylene-bridged polyphenylpolyamine mixtures by the condensation reaction of aniline and formaldehyde carried out at elevated temperatures in the presence of a silica-alumina cracking catalyst is well-known in the art and has been practiced commercially for many years. See for example U.S. Pat. No. 3,362,979 to Bentley. Generally speaking, such silica-alumina catalyzed aniline-formaldehyde condensation reaction procedures result in the production of methylene-bridged polyphenylpolyamine product mixtures containing a diamine portion, i.e., diaminodiphenyl methane, in the amount of from about 30 to about 92 weight percent and the remainder being higher molecular weight and higher functionality polymethylene polyphenylpolyamines (triamines, tetramines, etc.). As known, the amount of the diamine portion is dependent upon several processing variables, especially the molar ratio of aniline to formaldehyde employed. Usually at lower aniline-formaldehyde molar ratios, such as ratios of from about 1:1 to about 2.5:1, the higher functionality, molecular weight polyamines will be formed preferentially and the yield of higher polyamines is in excess to the yield of diamine. However, as progressively larger amounts of aniline are used, the yield of diamine is progressively increased at the expense of the higher functionality, molecular weight polyamine yield.

In addition, as known, the diamine portion of a polymethylene polyphenylpolyamine mixture produced by the silica-alumina catalyzed condensation reaction is formed as a mixture of the 2,2'-, 2,4'- and 4,4'-diamine positional isomers. The actual distribution between the positional isomer forms can be somewhat regulated by controlling processing variables such as temperature, method of addition of reactants and the like which are very well known. However, the diamine portion of such reaction product mixtures normally contains at least some portion of each positional isomer.

Diaminodiphenyl methane mixtures having high 4'-positional isomer content are particularly valuable materials as precursors for the preparation of corresponding methylene diphenylisocyanates which are useful in the preparation of certain types of coatings, elastomers and the like. Usually, such diaminodiphenyl methane materials are obtained from methylene-bridged polyphenylpolyamine reaction product mixtures prepared by the condensation reaction of aniline and formaldehyde carried out in the presence of a strong mineral acid catalyst, e.g., hydrochloric acid. Mineral acid catalyzed condensation reactions normally result in the production of aromatic polyamine reaction products having diamine portions which contain high amounts of the 4,4'-positional isomer. However, such mineral acid catalyzed condensation reaction procedures suffer from the disadvantage of requiring a neutralization step with a basic material, such as caustic, which accordingly brings on the difficulties of by-product removal and disposal. Moreover, mineral acids are generally highly corrosive and condensation reactions using them as catalysts require the utilization of expensive corrosive-resistant equipment such as glass-lined reactors and the like.

The above-mentioned silica-alumina catalyzed condensation reaction procedures do not require neutralization of the reaction product or the use of expensive corrosive-resistant equipment. However, it has heretofore been considered impossible to obtain a substantially pure diaminodiphenylmethane product containing substantially high levels of the 4,4'-positional isomer, e.g. above about 85 weight percent, basis diaminodiphenylmethane, from methylene-bridged polyphenylpolyamine mixtures produced by the aforementioned silica-alumina catalyzed condensation reaction. Experiments have shown that no more than about 92 weight percent diaminodiphenylmethane can be produced by the silica-alumina catalyzed condensation reaction no matter what molar ratios of aniline to formaldehyde are employed. Moreover, separation of high 4,4'-isomer-containing diaminodiphenylmethane product from such polyamine reaction product mixtures by distillation is very difficult and sacrificial. Such distillation techniques require the employment of expensive high vacuum distillation apparatus and subjecting the polyamine product mixtures to high temperatures. As known, polymethylene polyphenylpolyamines are susceptible to heat degradation. During such a high temperature distillation, these products have been found to degrade somewhat to aniline.

We have now discovered a process for obtaining substantially pure diaminodiphenylmethane mixtures containing substantially high amounts of the 4,4'-isomer form from certain methylene-bridged polyphenylpolyamine mixtures prepared by the silica-alumina catalyzed condensation reaction of aniline and formaldehyde. The discovery is believed to be a tremendous advance in the art inasmuch as it provides a technique for obtaining the desired, valuable high 4,4'-isomer containing methylene diphenylamines (diaminodiphenylmethane) product without encountering the disadvantages observed with mineral acid catalyzed condensation procedures. Moreover, the discovery provides enhanced flexibility for the use of polymethylene polyphenylpolyamine mixtures prepared by silica-alumina catalyzed condensation reaction procedures. Not only can substantially pure diaminodiphenylmethane products containing high levels of the 4,4'-isomer be obtained but also polymethylene polyphenylpolyamine mixtures of low diamine content and having narrow molecular weight distributions can be obtained which are useful as precursors for the preparation of corresponding polymethylene polyphenylisocyanates that can be employed in the production of specialty elastomers, coatings and the like.

SUMMARY OF THE INVENTION

In accordance with the present invention a methylene-bridged polyphenylpolyamine mixture, prepared by the condensation reaction of aniline and formaldehyde carried out at elevated temperature in the presence of a silica-alumina catalyst, containing at least about 75 weight percent isomeric diaminodiphenylmethanes with the remainder being higher functionality, higher molecular weight polymethylene polyphenylpolyamines, is admixed at a temperature of from about room temperature to about 150° C. with a solvent material capable of forming a solution with the polyphenylpolyamine mixture at a temperature within the aforesaid temperature range. A portion of the admixture-solution is then allowed to crystallize by conventional techniques such as by cooling or seeding. The crystallized portion is then separated whereby the crystallized portion has been found to be substantially pure diaminodiphenylmethanes having an increased 4,4'-positional isomer content of above about 85 weight percent basis diaminodiphenylmethane. Both the separated substantially pure diaminodiphenylmethanes and the polymethylene polyphenylpolyamine mixture filtrate, which has a reduced diaminodiphenylmethane content and a narrow molecular weight distribution of higher functionality polyamines are particularly valuable as precursors for preparing corresponding polyphenylpolyisocyanate mixtures useful in the production of specialty elastomers, coatings, and the like.

DETAILED DESCRIPTION OF THE INVENTION

Methylene-bridged polyphenylpolyamine mixtures that can be treated by the process of the invention are prepared by the well-known silica-alumina catalyzed condensation reaction of aniline and formaldehyde such as is described in U.S. Pat. No. 3,362,979, to Floyd E. Bentley, issued Jan. 9, 1968, which is incorporated herein by reference as if copied in full. The useful methylene-bridged polyphenylpolyamine mixtures are usually prepared by mixing and reacting about 5 to about 10 moles aniline per mole of formaldehyde in the presence of a silica-alumina cracking catalyst at a temperature of from about 170° to about 250° C., under a pressure of about 50 to about 300 psig. The resulting crude reaction product mixture is then preferably stripped of excess aniline and water of reaction and filtered to remove the catalyst by known distillation and filtration techniques as described in U.S. Pat. No. 3,362,979. The resulting polyamine mixture contains at least about 75 weight percent isomeric diaminodiphenyl methane which has a 4,4'-isomeric content of at least about 65 weight percent, basis the diamine portion.

Preferably, the methylene-bridged polyphenylpolyamine mixture has an average functionality of above about 2.0 to about 2.2 which contains from about 75 to about 95 weight percent diaminodiphenylmethane which has a 4,4'-isomer content of from about 65 to about 77 weight percent, a 2,4'-isomer content of from about 20 to about 30 weight percent, and a 2,2'-isomer content of from about 0 to about 5 weight percent, based upon the weight of the diaminodiphenylmethane portion. Such polyamine mixtures are readily available commercially under the trademark JEFFAMINE ® AP-21 from Jefferson Chemical Company, Inc., Houston, Tex.

For the purposes of brevity only, hereafter, methylene-bridged polyphenylpolyamine mixtures contemplated for use in the present invention will be referred to as "polyamine mixture(s)", diaminodiphenylmethane will be referred to as "diamine", and higher functionality, higher molecular weight polymethylene polyphenylpolyamines will be referred to as "higher polyamines".

In accordance with the present invention, the polyamine mixture is admixed with a solvent material capable of forming a solution with the polyamine mixture at a temperature of from about room temperature to about 150° C. which is selected from the group of consisting of an aromatic hydrocarbon, a halogen-substituted aromatic hydrocarbon and mixtures thereof. Preferably, the aromatic hydrocarbon is one containing from about 6 to about 10 carbon atoms per molecule and may include linear and/or branched alkyl groups. Examples of preferred aromatic hydrocarbons include benzene, toluene, xylene, ethylbenzene and the like. Preferred halogen-substituted hydrocarbons include the aforementioned aromatic hydrocarbons substituted with one to 3 halogen groups, particularly chlorine groups. Examples of prefered halogen-substituted aromatic hydrocarbons include monochlorobenzene, dichlorobenzene, mono- and dichlorotoluene, mono- and dichloroxylene, and the like.

We especially prefer to employ monochlorobenzene for admixture with the polyamine mixture. As known in the art, monochlorobenzene is a preferred solvent for the phosgenation of aromatic polyamines to prepare corresponding aromatic polyisocyanate materials utilizing conventional phosgenation techniques. Thus, by employing monochlorobenzene, the substantially pure diamine portion and the narrow molecular weight higher polyamine portions obtained by the process of the invention can be directly employed in conventional phosgenation procedures.

The polyamine mixture and solvent material are preferably admixed at a temperature of from about room temperature to about 150° C., the particular temperature employed being dependent upon the specific solvent material employed and that required to form a solution. Usually, a solution is formed at temperatures within the range of about 45° C. to about 75° C. when the above-mentioned solvent materials are utilized. Admixture and the desired temperature can be obtained by any conventional method. For example, the polyamine mixture and solvent material can be initially admixed at room temperature and, if required, the admixture can be heated until a solution is formed. Alternatively, the polyamine mixture or the solvent material, or both, can be heated individually and then admixed.

It is preferred to admix the polyamine mixture with the solvent material in concentrations within the range of about 20 to about 80 weight percent, based upon the total weight of materials. However, particular concentration within this range has not been to be critical in regard to the amount of diamine that can be obtained by the process of the invention.

A portion of the polyamine mixture-solvent material admixture-solution is then allowed to crystallize or precipitate by conventional techniques, such as by allowing the admixture-solution to cool or by seeding with pure 4,4'-diamine crystals. Usually, about 20 to about 50 weight percent of the polyamine mixture will crystallize out.

The crystallized portion or precipitate can be readily separated by any of the known conventional filtration techniques. Analysis of the crystallized portion has shown that it is substantially pure diamine (96–99 weight percent) having an increased 4,4'-positional isomer content of about 85–95 weight percent, basis diamine. As mentioned hereinbefore, the starting polyamine mixture employed usually contains about 65–77 weight percent 4,4'-isomer, basis weight of diamine portion.

An additional advantage of the process of the invention, as mentioned hereinbefore, is the fact that the filtrate contains higher polyamines having a narrow molecular weight range with a reduced level of diamine content. Heretofore, it was considered impractical to prepare such materials by the aforementioned conventional silica-alumina catalyzed condensation reaction of aniline and formaldehyde for the resulting reaction product contained too many solids when dissolved in chlorobenzene and readied for processing in conventional phosgenation techniques. Surprisingly, the filtrate of the process of the invention can be diluted with chlorobenzene to an appropriate concentration without solids formation and thus be utilized as is in such phosgenation techniques. Corresponding polyisocyanates prepared from the filtrate having a narrow molecular weight distribution and low diamine content are particularly valuable for the production of specialty coatings, elastomers, etc.

The objectives of the present invention are accomplished by the employment of the aforementioned polyamine mixtures that contain at least about 75 weight percent diamine. Most unexpectedly, experiments have shown that polyamine mixtures containing less than about 75 weight percent diamine, prepared by the same silica-alumina catalyzed condensation reaction of aniline and formaldehyde, do not result in the formation of any significant portion of crystallized substantially pure diamines in accordance with the present invention, as illustrated in the following examples. In fact, it has been observed that the solubility of such polyamine mixtures increase with increasing concentrations when treated in accordance with the present invention.

EXAMPLE I 30 g. of a methylene-bridged polyphenylpolyamine mixture containing 88 weight percent diaminodiphenylmethanes of which 73 weight percent was the 4,4'-isomer, 23 weight percent was the 2,4'-isomer and 4 weight percent was the 2,2'-isomer, basis weight of diamine, (prepared by the silica-alumina condensation reaction of aniline and formaldehyde; JEFFAMINE ® AP-21, Jefferson Chemical Company, Inc., Houston, Tex.) was heated to about 75° C. and then added with stirring to 70 g. warm monochlorobenzene (50° C.). The resulting clear solution was allowed to stand overnight whereby a portion thereof crystallized or precipitated. The solids were collected, washed with cold monochlorobenzene and ether and dried. The dried solids weighed 9.3 g. Analysis of the solids showed they comprised 99.1 weight percent diaminodiphenylmethane which contained 93 weight percent 4,4'-isomer, 6 weight percent 2,4'-isomer, and 1 weight percent 2,2'-isomer, basis diaminodiphenylmethane present.

EXAMPLE II 40 g. of the methylene-bridged polyphenylpolyamine mixture described in Example I, heated to 75° C., was added to 60 g. of warm monochlorobenzene (50° C.) with stirring and the clear solution was allowed to stand overnight. The solids formed were collected, washed and analyzed as described in Example I. Analysis showed the solids were 96 weight percent diaminodiphenylmethane which has a positional isomer distribution of 87 weight percent 4,4'-, 12 weight percent 2,4'- and 1 weight percent 2,2'-isomers. The solids isolated weighed 15.9 g. (dried basis) which amounted to approximately 40 weight percent of the polyamine mixture starting material.

EXAMPLE III

To 50 g. of warm benzene (50° C.) was added, with stirring, 50 g. of the methylene-bridged polyphenylpolyamine mixture starting material described in Example I, heated to 75° C. The resulting clear solution was allowed to stand overnight whereby a portion thereof crystallized or precipitated. The precipitated solids were collected, washed with cold monochlorobenzene and ether and dried. The dried solids weighed 18.1 g. which amounted to 36.2 weight percent of the polyamine starting material. Analysis of the solids showed they comprised 96.7 weight percent diaminodiphenylmethane having an isomer distribution of 89 weight percent 4,4'-, 10 weight percent 2,4'- and 1 weight percent 2,2'-isomers.

EXAMPLE IV

In this example, two related methylene-bridged polyphenylpolyamine mixtures, each prepared by the silica-alumina catalyzed condensation reaction of aniline and formaldehyde, were treated in accordance with the inventive procedure. One sample, identified as Sample 1 in the following Table 1, had an average functionality of about 2.4, contained about 69.1 weight percent diaminodiphenylmethane which had an isomer content of about 74.7 weight percent 4,4'-, 21.9 weight percent 2.4'- and about 3.4 weight percent 2,2'- isomers, basis diamine portion, and the remainder higher functionality, higher molecular weight polyamines (JEFFAMINE ® AP-22, Jefferson Chemical Company, Inc.). The second sample, identified as Sample 2 in the following Table 1, had an average functionality of about 2.7 and contained about 50 weight percent diaminodiphenylmethane, the remainder being higher functionality, higher molecular weight polyamines. The diamine portion thereof had an isomer distribution of about 74.3 weight percent 4,4'-, 22.1 weight percent 2,4'- and 3.6 weight percent 2,2'- isomers (JEFFAMINE ® AP-27, Jefferson Chemical Company, Inc.). The two samples were separately admixed with monochlorobenzene at room temperature in varying concentrations as set forth in the following Table 1 and allowed to stand overnight. As shown in Table 1, the only precipitated or crystallized solids observed in either treated sample were at polyamine concentrations of 30% or below. However, these solids comprised an inseparable mixture of higher molecular weight polyamines, not substantially pure diaminodiphenylmethane.

TABLE 1

| Concentration of Polyamine in Monochlorobenzene (wt.%) | Sample 1 | Sample 2 |
| --- | --- | --- |
| 5% | lt.[2]color solids | lt. color solids |
| 10% | drk.[3]solids, sl.[4] more | dk. solids, sticky |
| 20% | few solids, haze | solids, fewer |
| 30% | no solids, only haze | few solids, slight haze |
| 40% | clear, no solids, no ppt[5] | almost clear |
| 50% | clear, no solids, no ppt | clear, no solids, no ppt |
| 60 | clear, no solids, no ppt | clear, no solids no ppt |
| 70% | clear, no solids, no ppt | clear, no solids, no ppt |
| 80% | clear, no solids, no ppt | clear, no solids, no ppt |
| 90% | clear, no solids, | clear, no solids, |

TABLE 1-continued

| Concentration of Polyamine in Monochlorobenzene (wt.%) | Sample 1 | Sample 2 |
|---|---|---|
| | no ppt | no ppt |

[1] after standing overnight
[2] light
[3] dark
[4] slightly
[5] precipitate

A comparison of the results of Table 1 to the results of Examples I-III illustrate the unexpected results of the present invention. The polyamine mixture starting material in Examples I-III and those described in Example IV are prepared by substantially the same silica-alumina catalyzed condensation reaction of aniline and formaldehyde. However, the polyamine mixture described in Examples I-III has the higher diaminodiphenylmethane content from which substantially pure diaminodiphenylmethane having a higher 4,4'-content could be separated. Unexpectedly, even at low concentrations of polyamine mixture-solvent material, no diaminodiphenylmethane could be separated by the process of the invention from the related polyamine mixtures described in Example IV.

Having thus described my invention, what is claimed is:

1. An improved process for the separation of low functionality substantially pure diaminodiphenylmethanes containing increased 4,4'-isomer contents from methylene-bridged polyphenylpolyamine mixtures prepared by the catalyzed condensation reaction of aniline and formaldehyde carried out in the presence of a silica-alumina catalyst, said process comprising:

admixing, at a temperature of from about room temperature to about 150° C., a methylene-bridged polyphenylpolyamine mixture containing at least 75 weight percent diaminodiphenylmethane having a 4,4'-isomer content of above about 65 weight percent, based upon the weight of said diaminodiphenylmethane, with the remainder being higher molecular weight, higher functionality methylene-bridged polyphenylpolyamines, with a solvent material capable of forming a solution with said methylene-bridged polyphenylpolyamine mixture at said temperature of from about room temperature to about 150° C., said solvent material being selected from the group consisting of an aromatic hydrocarbon, a halogen-substituted aromatic hydrocarbon and mixtures thereof;

allowing a portion of the admixture to crystallize; and separating the crystailized portion, said crystallized portion comprising substantially pure isomeric diaminodiphenylmethane having an increased 4,4'-isomer content above about 85 weight percent, based upon the weight of diaminodiphenylmethane present.

2. The process in accordance with claim 1 wherein said aromatic hydrocarbon has 6 to about 10 carbon atoms per molecule.

3. The process in accordance with claim 2 wherein said aromatic hydrocarbon is one selected from the group consisting of benzene, toluene, xylene, ethylbenzene, and mixtures thereof.

4. The process in accordance with claim 1 wherein said halogen-substituted aromatic hydrocarbon is a chlorine-substituted hydrocarbon having about 6 to about 10 carbon atoms substituted with 1 to 3 chlorine groups.

5. The process in accordance with claim 4 wherein the chlorine-substituted aromatic hydrocarbon is selected from monochlorobenzene, dichlorobenzene, monochloroxylene, dichloroxylene, monochlorotoluene, dichlorotoluene or mixtures thereof.

6. The process of claim 1 wherein said methylene-bridged polyphenylpolyamine mixture is admixed with said solvent mixture in a concentration of from about 20 to about 80 weight percent, based upon the total weight of the admixture.

7. The process in accordance with claim 1 wherein said methylene-bridged polyphenylpolyamine mixture admixed with said solvent material contains from about 75 to about 92 weight percent isometric diaminodiphenylmethane.

* * * * *